United States Patent [19]
Tseng

[11] Patent Number: 5,619,287
[45] Date of Patent: Apr. 8, 1997

[54] EYEGLASSES WITH A REPLACEABLE SUNSHADE

[76] Inventor: Liang-Chin Tseng, 1-3, Shih-Fen Tsun, Chi-Ku Hsiang, Tainan Shien, Taiwan

[21] Appl. No.: 377,058

[22] Filed: Jan. 23, 1995

[51] Int. Cl.$^6$ .................................................. G02C 7/10
[52] U.S. Cl. .............. 351/44; 351/86; 351/124; 351/155; 351/158; 2/10
[58] Field of Search ................... 351/44, 85, 83, 351/86, 88, 140, 141, 158, 155, 147, 41, 47, 57, 136, 153; 2/426, 427, 431, 432, 439, 10

[56] References Cited
U.S. PATENT DOCUMENTS

| | | | |
|---|---|---|---|
| 2,700,765 | 12/1952 | Hoffmaster | 351/44 |
| 3,233,250 | 7/1963 | Jonassen | 351/44 |
| 5,335,025 | 8/1994 | Wang | 351/47 |

*Primary Examiner*—William L. Sikes
*Assistant Examiner*—Hung Xuan Dang

[57] ABSTRACT

A pair of eyeglasses with a sunshade comprising a sunshade releasably combined with a frame and a plate glass also collapsibly combined with the frame, the sunshade and the plate glass being replaceable to be combined with the frame according to the taste of a user.

3 Claims, 3 Drawing Sheets

EYEGLASSES WITH A REPLACEABLE SUNSHADE

BACKGROUND OF THE INVENTION

This invention concerns a pair of eyeglasses with a sun-shade, particularly one having its sunshade replaceable, and its plate glass also replaceable.

At present, most eyeglasses with a sunshade are generally not collapsible, not quite convenient for carrying.

SUMMARY OF THE INVENTION

An object of the present invention is offer a kind of eyeglasses with a replaceable sunshade and collapsible for carrying convenience.

A main feature of this invention is a frame having an upper lengthwise aperture in an upper intermediate portion for releasably combining a bridge, lengthwise fitting groove respectively extending from under the two ends of the upper aperture to the right and the left in a front side, and a lengthwise lower groove facing down in a lower side for combining a plate glass. The bridge has an upper horizontal portion provided with an inverted U-shaped groove defined by a front wall, which fits in the upper aperture of the frame.

DETAILED DESCRIPTION OF THE INVENTION

Figure 1:
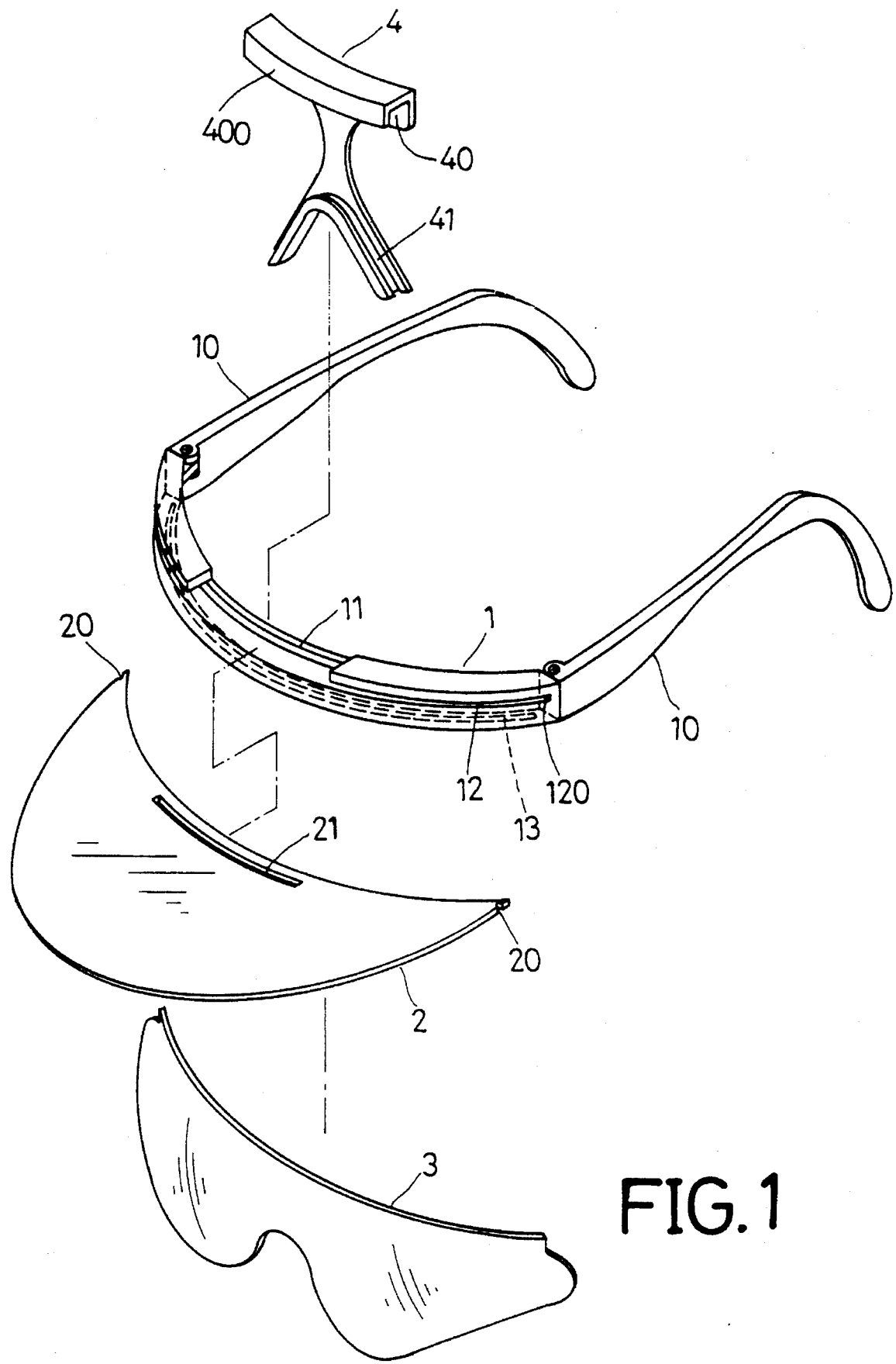
FIG. 1 is an exploded perspective view of a pair of eyeglasses with a sunshade in the present invention.

A pair of eyeglasses with a sunshade in the present invention, as shown in FIGS. 1, comprises a frame 1, a sunshade 2, a plate glass 3 and a bridge 4 as main components combined together.

The frame 1 has two temples 10, 10 connected with two ends of the frame 1, a lengthwise aperture 11 in an upper surface of an intermediate portion, a lengthwise fitting groove 12 respectively extending in a front side from under two ends of the lengthwise aperture 11 to the right side and the left side, a pointed projection 120 at the end of each fitting groove 12, and another lengthwise fitting groove 13 facing down in a lower surface.

The sunshade 2 has an inner side curved as the curvature of the frame 1 to fit firmly in the two lengthwise fitting grooves 12, 12 of the frame 1, a notch 20 respectively in two ends of the inner curved side, and a curved slot 21 almost parallel to and near the inner curved side edge.

The plate glass 3 has its upper side fitting in the fitting groove 13 of the frame 1, made integral as one piece.

The bridge 4 has a horizontal portion to fit in the lengthwise aperture 11 of the frame 1, a lengthwise aperture 40 facing down in the horizontal portion and defined by a front wall 400, and a forked portion with a fitting groove 41 facing up and sloping down from its center to two sides.

Figure 2:
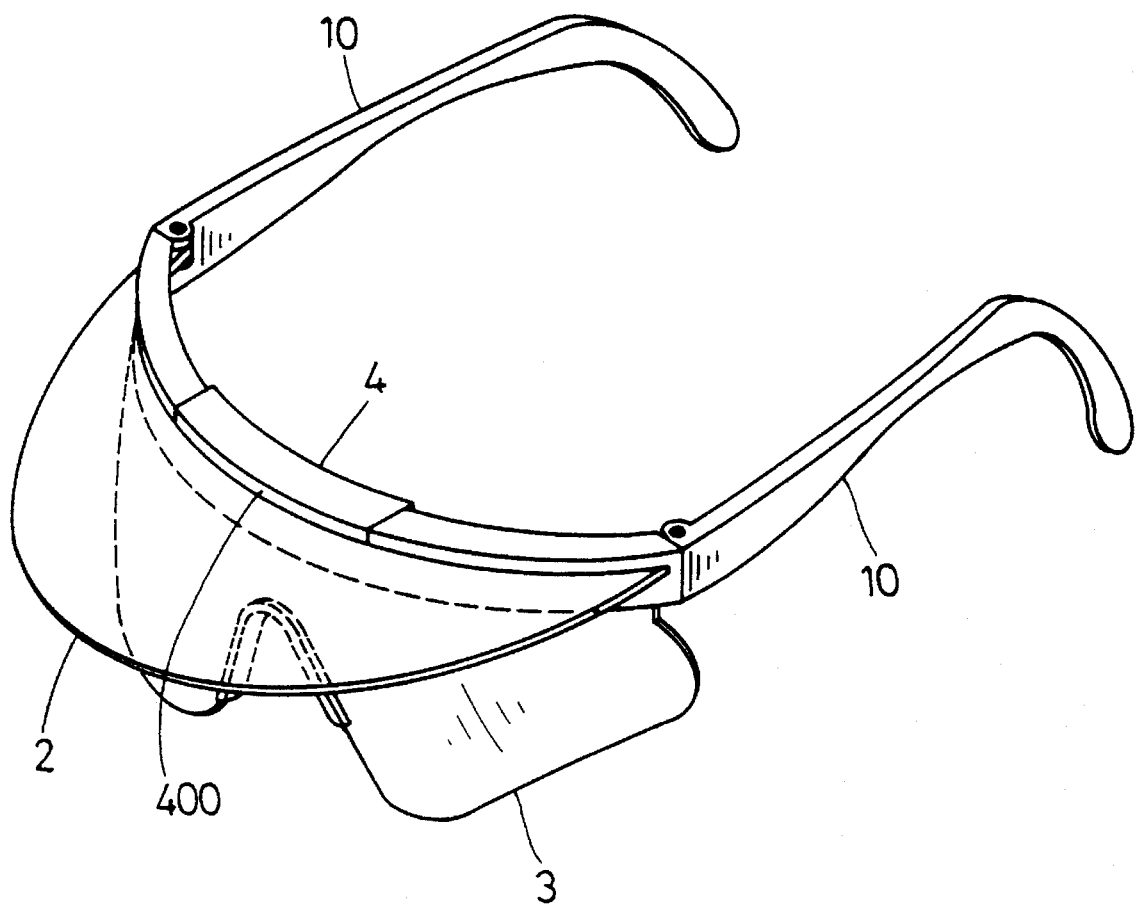
FIG. 2 is a perspective view of the pair of eyeglasses with a sunshade in the present invention.
Figure 3:
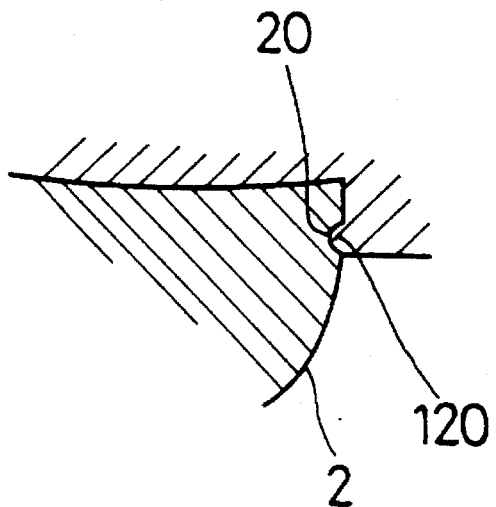
FIG. 3 is a cross-sectional view of a sunshade combined with a frame in the present invention.
Figure 4:
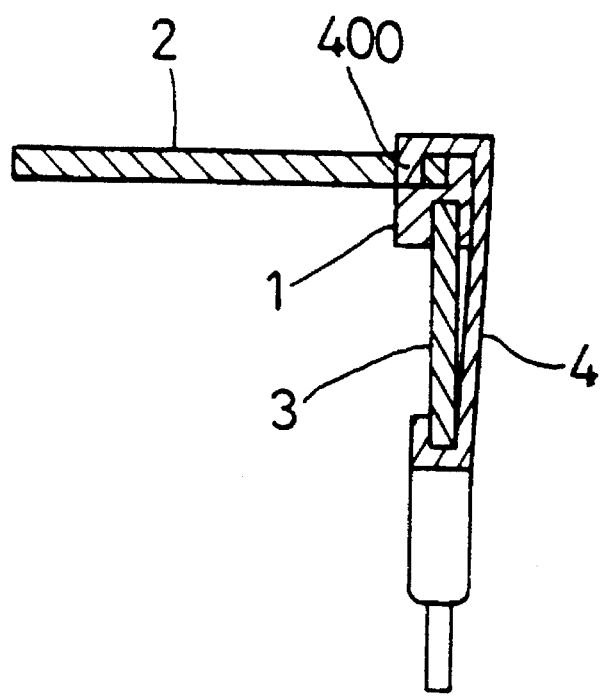
FIG. 4 is a cross-sectional view of the sunshade combined with the frame in another way in the present invention.

In assembling, referring to FIGS. 2, 3 and 4, firstly the sunshade 2 is made to fit in the fitting grooves 12, 12 of the frame 1, with the two pointed projections 120, 120 of the grooves 12, 12 fitting in the two notches 20, 20 of the sunshade 2 to keep the sunshade 2 from falling off. Secondly, the upper side of the plate glass 3 is made to fit in the fitting groove 13 of the frame 1, and then the bridge 4 is combined with the frame 1, with the lengthwise aperture 40 facing with the lengthwise groove 11, and with the front lengthwise wall 400 fitting in the slot 21 of the sunshade 2. Thus, the sunshade 2 is pivotally combined with the frame 1 very stably. Lastly, the plate glass 3 is combined with the bridge 4, with the lower center portion of the plate glass 3 fitting in the fitting groove 41 of the bridge, finishing the assemblage.

In using, a user can select to use a variety of the sunshades 2 and the plate glasses 3 to combine with the frame 1. In taking down a plate glass 3 already combined with the frame 1, the plate glass 3 is pulled out of the fitting groove 41 of the bridge 4 at first, and then the front wall 400 of the bridge 4 is pulled out of the slot 21 of the sunshade 2, permitting the plate glass 3 disengage from the frame 1. After that, the sunshade 2 can be taken off the grooves 12, 12 of the frame i. Then a newly selected sunshade 2 and a newly selected plate glass 3 can be combined with the frame 1 in the way described above.

It may be understood that this invention has advantages as follows.

1. A variety of sunshades and plate glasses can be selectably used to give different color and decoration to the eyeglasses according to the taste of a user.

2. It is convenient for carrying, collapsible to become of small dimensions.

What is claimed is:

1. An eyeglasses with a sunshade comprising:

a frame having a lengthwise aperture in an upper surface of an intermediate portion, and a lengthwise fitting groove respectively in a lower portion extending from under two ends of said lengthwise aperture to the right and the left side;

a sunshade combined with the frame, with its inner curved side having the same curvature of said frame and fitting in said two lengthwise fitting grooves of said frame, having a slot parallel to and near the inner curved side edge;

a plate glass made as one piece and combined with said frame, fitting in a lower side of said frame;

a bridge having an upper horizontal portion and a lower forked portion extending down from the upper horizontal portion, said horizontal portion having an inverted U-shaped aperture facing down and defined by a front wall;

said sunshade being replaceable, with its inner curved side releasably fitting in said two lengthwise fitting grooves of said frame, for easy and fast collapsing.

2. The eyeglasses with a sunshade as claimed in claim 1, wherein said frame further has a lengthwise groove facing down in a lower side.

3. The eyeglasses with a sunshade as claimed in claim 1, wherein said two lengthwise grooves of said frame have a pointed projection respectively at their ends.

* * * * *